(12) United States Patent
Marton et al.

(10) Patent No.: US 12,357,218 B2
(45) Date of Patent: Jul. 15, 2025

(54) ELECTROCARDIOGRAM LEAD GENERATION

(71) Applicant: The Vektor Group Inc., San Diego, CA (US)

(72) Inventors: Christian David Marton, Jersey City, NJ (US); Joseph Thomas Braidwood, Carlsbad, CA (US); Robert Joseph Krummen, Bellevue, WA (US); Maurice J. Pirio, Seattle, WA (US)

(73) Assignee: THE VEKTOR GROUP, INC., San Diego, CA (US)

( * ) Notice: Subject to any disclaimer, the term of this patent is extended or adjusted under 35 U.S.C. 154(b) by 0 days.

(21) Appl. No.: 18/887,328

(22) Filed: Sep. 17, 2024

(65) Prior Publication Data

US 2025/0009274 A1    Jan. 9, 2025

Related U.S. Application Data

(62) Division of application No. PCT/US2023/075742, filed on Oct. 2, 2023.

(60) Provisional application No. 63/412,830, filed on Oct. 3, 2022.

(51) Int. Cl.
*A61B 5/319* (2021.01)
*A61B 5/339* (2021.01)
*A61B 5/367* (2021.01)

(52) U.S. Cl.
CPC .............. *A61B 5/319* (2021.01); *A61B 5/339* (2021.01); *A61B 5/367* (2021.01); *A61B 2560/0223* (2013.01)

(58) Field of Classification Search
CPC ................ A61B 5/319; A61B 5/339

USPC ......................................... 600/509
See application file for complete search history.

(56) References Cited

U.S. PATENT DOCUMENTS

| | | |
|---|---|---|
| 5,058,598 A | 10/1991 | Nicklas et al. |
| 2002/0035334 A1 | 3/2002 | Meij et al. |
| 2015/0208936 A1 | 7/2015 | Young et al. |
| 2019/0328457 A1* | 10/2019 | Villongco ................ A61B 5/35 |

(Continued)

FOREIGN PATENT DOCUMENTS

WO    2022014943 A1    1/2022

OTHER PUBLICATIONS

Dosovitskiy, A., et al., An Image is Worth 16×16 Words: Transformers for Image Recognition at Scale, Published as a conference paper at ICLR 2021, 22 pages.

(Continued)

*Primary Examiner* — Nadia A Mahmood
(74) *Attorney, Agent, or Firm* — Perkins Coie LLP

(57) ABSTRACT

Systems are provided for synthesizing leads of an electrocardiogram (ECG) based on a subject ECG collected from a subject and converting a nonstandard ECG based on a nonstandard placement of electrodes to a standard ECG with a standard placement of electrodes. The described systems may generate simulated ECGs based on simulations of electrical activity of hearts having different heart configurations. From each simulation, simulated ECGs are generated assuming a specification of electrode position(s) for each lead of an ECG. The systems identify a simulated ECG that is similar to the subject ECG. Based on the simulation from which that simulated ECG was generated, the systems identify a synthesized ECG or converted ECG.

16 Claims, 8 Drawing Sheets

(56) References Cited

U.S. PATENT DOCUMENTS

2019/0333643 A1   10/2019   Villongco
2020/0175688 A1    6/2020   Krummen et al.

OTHER PUBLICATIONS

Kors, J.A., et al., "Reconstruction of the Frank vectorcardiogram from standard electrocardiogramads: diagnostic comparison of different methods," European Heart Journal, vol. 11, Issue 12, Dec. 1, 1990, pp. 1083-1092.

Krasteva, V., et al., "Simulating Arbitrary Electrode Reversals in Standard 12-Lead ECG," Sensors, Jul. 1, 2019, 19, 2920, 19 pages.

Nelwan, SP, et al., "Correction of ECG Variations Due to Non-Standard Electrode Positions," IEEE, Computers in Cardiology, 2001;28::317-319.

Tiu, E., et al., "Expert-level detection of pathologies from unannotated chest X-ray images via self-supervised learning," Nature Biomedical Engineering, 11 pages, https://doi.org/10.1038/s41551-022-00936-9.

Trayanova, N. A., "Whole-Heart Modeling Applications to Cardiac Electrophysiology and Electromechanics," Circresaha, Circulation Research, Jan. 7, 2011, pp. 113-128.

International Search Report and Written Opinion received in Application No. PCT/US23/75742, dated May 15, 2024, 21 pages.

* cited by examiner

ELECTROCARDIOGRAM LEAD GENERATION

CROSS-REFERENCE TO RELATED APPLICATION(S)

This application is a continuation of International Application No. PCT/US23/75742, titled "ELECTROCARDIOGRAM LEAD GENERATION" and filed on Oct. 2, 2023, which claims the benefit of priority to U.S. Provisional Application No. 63/412,830, titled "BODY COMPOSITION ECG PROCESSING SYSTEM" and filed on Oct. 3, 2022, the entire disclosure of each of these applications is incorporated herein by reference.

BACKGROUND

Cardiologists rely on visual inspections of electrocardiograms (ECGs) for diagnosing a variety of cardiac conditions such as an arrhythmia, cardiomyopathy, ST-Elevated Myocardial Infarction (STEMI), and so on. Cardiologists typically are presented with a 12-lead ECG based on 10 electrodes with standard placements on the chest and limbs. Cardiologists are experts at interpreting 12-lead ECGs and developing treatments based on those interpretations. However, many ECG acquisition devices, such as Holter monitors, 3-lead patches, smartwatches, and smartphones, do not generate 12-lead ECGs. Moreover, some of the leads that are generated may not correspond directly or accurately to any of the 12 leads. Even when a 12-lead ECG is generated, it may be generated based on electrodes with nonstandard placements. In such a case, the nonstandard placement 12-lead ECG will be somewhat different from the standard placement 12-lead ECG. When presented with fewer leads or leads based on nonstandard placements, cardiologists may arrive at interpretations that are somewhat different from the interpretations that they might have made if presented with a standard placement 12-lead ECG. As a result, the diagnosis and corresponding treatment may be less than optimal. Various software tool have been developed to process one or more leads of a 12-lead ECG to, for example, generate an arrhythmia classification (e.g., atrial fibrillation or atrial flutter), identify a source location of an arrhythmia, or identify a type of myocardial infarction (e.g., STEMI). When processing a lead that does not correspond to a standard placement, the diagnosis and treatment may similarly be less than optimal.

The ability for people to collect their own ECGs has increased because some personal mobile devices, such as smartwatches and smartphones, are equipped with or interface with a personal ECG acquisition device. A smartwatch may collect a one-lead ECG (e.g., lead I) using an electrode that contacts the arm under the smartwatch and another electrode that contacts a finger on the hand of the other arm. A smartphone may be adapted to interface with a personal ECG acquisition device that collects a multi-lead ECG based on electrodes (typically less than 10) placed by the user. An ECG application executing on the smartphone receives the multi-lead ECG (e.g., via a USB-C or Bluetooth connection). These personal mobile devices can display the ECG and also transmit it to a medical provider. The ECGs collected by such personal mobile devices, however, are not as accurate as ones collected by a medical-grade ECG acquisition device (e.g., MAC 2000), in part because the electrode placement may be nonstandard.

To assist in the correct placement, an ECG application may have a training mode to train a subject on the correct placement of the electrodes. Although training can be helpful, it is still very common for the electrodes to be misplaced. Even a trained medical provider may place electrodes at nonstandard locations, especially in emergency situations where the subject may have injuries near a standard location or where the standard location is inaccessible. (See Wenger, W., and Kligfield, P., "Variability of Precordial Electrode Placement During Routine Electrocardiography," Journal of Electrocardiology, vol. 29, iss. 3, pp. 179-184, 1996.) For example, a 3-lead patch (e.g., with five electrodes) has a standard location for each of the electrodes. The actual placement of the electrodes of the patch, however, may be at nonstandard locations because the patch is horizontally, vertically, or rotationally offset from its ideal placement. The horizontal and vertical offsets may be even greater if the ECG device has electrodes that are to be independently placed. As another example, an ECG T-shirt or an ECG chest strap can generate ECGs with, for example, one or 12 leads. However, some of the electrodes may be at nonstandard locations. For example, electrodes of an ECG T-shirt cannot be placed on the legs or arms, and an ECG chest strap is typically worn below the standard locations of the precordial electrodes.

Some attempts have been made to convert a reduced-lead ECG to a 12-lead ECG and to correct for nonstandard placement of electrodes. One technique for converting a reduced-lead ECG to a 12-lead ECG collects a 12-lead ECG and a 3-lead ECG from a subject, generates a linear transformation from the 3-lead ECG to the 12-lead ECG, and applies the transformation to another 3-lead ECG to generate the corresponding 12-lead ECG. (See U.S. Pat. Pub. No. 2023/0106036, titled "Method and Apparatus for Reconstructing Electrocardiogram (ECG) Data" and published on Apr. 6, 2023; U.S. Pat. No. 5,058,598, titled "Method and Apparatus for Synthesizing Leads of an Electrocardiogram" and issued on Oct. 22, 1991; and Newlan, S., et al., "Reconstruction of the 12-Lead Electrocardiogram from Reduced Lead Sets," Journal of Electrocardiology, vol. 37, iss. 1, pp. 11-18, 2004.) One technique for correcting for nonstandard placement generates subject-specific reconstruction coefficients for mapping the nonstandard placement ECG to the standard placement ECG and then applying the mapping to another nonstandard placement ECG to generate the corresponding standard placement ECG.

DETAILED DESCRIPTION

ECG Processing System

Figure 1:
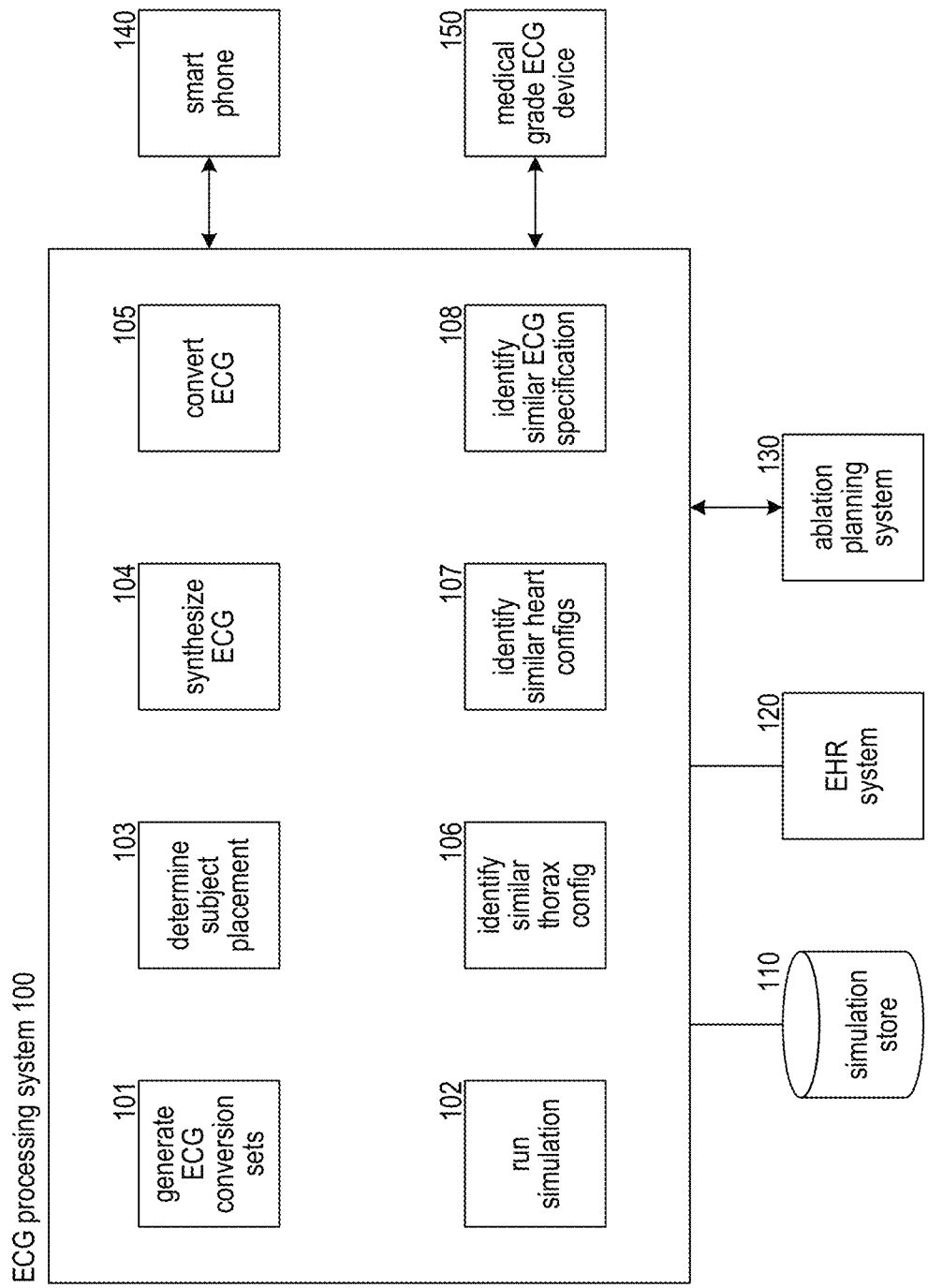
FIG. 1 is a flow diagram that illustrates components of an ECG processing system in some embodiments.

An ECG processing system is provided that synthesizes a lead from one or more leads of a source ECG and/or converts an ECG having a source placement to an ECG having a target placement. In some embodiments, an ECG synthesis system of the ECG processing system inputs a source ECG and outputs a synthesized ECG having one or more leads that are synthesized based on the source ECG. For example, a source ECG may be a 3-lead ECG, and the synthesized ECG may be a 12-lead ECG. As another example, a source ECG may have only 11 out of 12 standard leads (e.g., because of an electrode not being in full contact with the skin), and the synthesized ECG may be the missing 1-lead ECG. An ECG conversion system of the ECG processing system inputs a source ECG with a source placement and outputs a corresponding converted ECG with a different (e.g., corrected) placement. For example, the source ECG may be a standard placement 12-lead ECG, and the converted ECG may be a nonstandard placement 12-lead ECG (e.g., for comparison to another nonstandard placement ECG). As another example, the source ECG may be a nonstandard placement 3-lead ECG, and the converted ECG may be a standard placement 3-lead ECG.

Given a source ECG that is to be converted to a different placement and also have a lead synthesized, the ECG processing system may be used to synthesize the lead and convert the source ECG to a converted ECG with the different placement. For example, the source ECG may be an 11-lead ECG with a nonstandard placement, and the converted ECG may be a 12-lead ECG with a standard placement. To both synthesize and convert, the lead may first be synthesized based on the source ECG, and then the source ECG and the synthesized lead may be converted to a converted ECG. Alternatively, the source ECG may first be converted to a converted ECG, and then the lead may be synthesized from the converted ECG.

The ECG processing system may also interface with medical systems to retrieve and/or store information. For example, the ECG processing system may provide a synthesized and/or a converted ECG to an arrhythmia mapping system that identifies a probable source location of an arrhythmia and suggests an ablation pattern to use in an ablation procedure. (See U.S. Pat. No. 10,860,754, titled "Calibration of Simulated Cardiograms" and issued on Dec. 8, 2020, which is hereby incorporated by reference.) As another example, the ECG processing system may retrieve a subject ECG from a medical-grade ECG acquisition device during an ablation procedure. As another example, the ECG processing system may interface with an electronic health record (EHR) system to retrieve a subject ECG and to store a converted ECG.

In the following, embodiments of the ECG processing system are described as synthesizing a standard ECG (e.g., 12-lead) from a reduced-lead ECG (e.g., 3-lead) and as converting a nonstandard placement ECG to a standard placement ECG. But the ECG processing system may be employed to synthesize and convert source ECGs with any source number of leads having any placement to an ECG with any number of leads having any placement. The techniques of the ECG processing system may also be employed to process electrograms of other organs (e.g., a gastroenterogram of a gastrointestinal tract) and to process other types of cardiograms (e.g., a vectorcardiogram).

An ECG may be represented as an image or a voltage-times series. If represented as an image, the ECG may be converted to a voltage-time series. An image may be converted, for example, by taking a picture or screenshot of a displayed ECG or taking a picture of a printed ECG. Techniques for converting an image of an ECG to a voltage-time series are described in U.S. patent application Ser. No. 17/865,249, titled "Encoding Electrocardiogramata" and filed on Jul. 14, 2022.

ECG Synthesis System

The ECG synthesis system automatically synthesizes (e.g., generates or identifies) a target lead ECG (i.e., a synthesized ECG) with a certain number of leads (t leads), referred to as a t-lead ECG, given a source lead ECG with a certain number of leads (s leads), referred to as an s-lead ECG, where s and t represent the number of leads. The ECG synthesis system runs simulations of electrical activity of a heart where each simulation is based on a heart configuration with a different set of heart characteristics. The heart characteristics include various anatomical and electrophysiological characteristics of a heart. The anatomical characteristics may relate to shape, orientation, scar tissue, prior ablations, and so on. The electrophysiological characteristics may relate to conduction velocity, action potential, regions of abnormal electrical activity (e.g., source of an arrhythmia), and so on. A simulation may be run to generate, for example, 30 seconds of electrical activity (e.g., covering 30 cardiac cycles) at intervals of one millisecond to represent the electrical activity at those intervals. Techniques for running such simulations are described in U.S. Pat. No. 10,860,754 and Trayanova, N., "Whole-Heart Modeling: Applications to Cardiac Electrophysiology and Electromechanics," Circulation Research 108, no. 1 (2011): 113-128, which are hereby incorporated by reference.

From the simulated electrical activity of each simulation, the ECG synthesis system generates simulated ECGs assuming different thorax configurations and different ECG specifications. A thorax configuration specifies thorax characteristics such as body size and body composition. Body composition includes fat and muscle characteristics (e.g., distribution), bone density, and so on. An ECG specification specifies a number of leads (e.g., 3, 5, 8, or 12) and, for each lead, the location of one or more electrodes used to generate that lead (e.g., right wrist and left finger employed by a smartwatch to generate a single lead or 10 standard locations employed by a 12-lead ECG acquisition device). The ECG synthesis system maintains, for each simulated ECG, an association between the heart configuration of the simulation from which it was generated and the thorax configuration and the ECG specification based on which it was generated. As an example of the number of simulated ECGs that would be generated, if there are 1,000 different heart configurations, 10 different ECG specifications, and 5 different thorax configurations, the ECG synthesis system would generate 50,000 simulated ECGs. As another example, if the ECG synthesis system synthesizes, based on a standard thorax, a standard 12-lead ECG and a standard 3-lead ECG for each of 1,000 heart configurations, the ECG synthesis system would generate 2,000 ECGs.

When the ECG synthesis system is provided an s-lead ECG of a subject (e.g., patient or other person), the ECG synthesis system identifies a simulated s-lead ECG based on similarity to the subject s-lead ECG. The ECG system then outputs an indication of the simulated t-lead ECG generated from the same simulation assuming the same thorax configuration.

If the subject body configuration (e.g., all or a portion of the heart configuration and/or thorax configuration) is available, the ECG synthesis system may use the subject body configuration to calibrate the simulations. Some of the thorax configuration (e.g., body composition and thorax shape) may be derived from data collected by the body composition estimate system that is described below. In some embodiments, to perform the calibration based on both the subject heart configuration and the subject thorax configuration, the ECG synthesis system identifies simulations that were based on simulated heart configurations that are similar to the subject heart configuration. From those identified simulations, the ECG synthesis system identifies simulated ECGs that were based on simulated thorax configurations that are similar to the subject thorax configuration. The identified simulated ECGs are calibrated simulated ECGs. The ECG system then identifies, from the calibrated ECGs, a simulated s-lead ECG based on similarity to the subject s-lead ECG. The ECG synthesis system then identifies a simulated t-lead ECG generated from the same simulation as and based on the same thorax configuration as that identified simulated s-lead ECG. The ECG synthesis system then outputs an indication of the identified simulated t-lead ECG as a representation of the subject t-lead ECG derived from the subject s-lead ECG.

In some embodiments, the ECG synthesis system may dynamically generate a simulated s-lead ECG and a simulated t-lead ECG based on their ECG specifications and the subject thorax configuration. Thus, the ECG synthesis system would generate two simulated ECGs for each simulation. If the subject heart configuration is known, the ECG synthesis system may identify the simulations that are based on simulated heart configurations that are similar to the subject heart configuration (e.g., calibrate the simulations) and generate simulated ECGs based on only those simulations and based on the ECG specifications. For example, if the simulated heart configurations of 30 simulations are similar to the subject heart configuration, then the ECG synthesis system would generate 60 simulated ECGs. Since the number of simulated ECGs that need to be generated is small, the ECG synthesis system may synthesize a subject t-lead ECG given a subject s-lead ECG in real time and provide very quick feedback to the subject or a medical provider.

In some embodiments, if the subject heart configuration, thorax configuration, and ECG specifications for the s-lead ECG and the t-lead ECG are known in advance, the ECG synthesis system may pre-generate the simulated s-lead ECGs and simulated t-lead ECGs. In such a case, when the subject s-lead ECG is collected, the ECG synthesis system need only compare the subject s-lead ECG to the pre-generated simulated s-lead ECGs and select the associated simulated t-lead ECG to represent the subject t-lead ECG. Because the simulated s-lead ECGs and the simulated t-lead ECGs are pre-generated, the feedback may be even quicker.

In some embodiments, however, the ECG synthesis system may perform a more in-depth processing when generating a t-lead ECG for a medical provider. For example, the medical provider may not need the t-lead ECG to be provided for a few hours or days after the s-lead ECG is collected, such as by the time of the next scheduled appointment. The more in-depth processing may include running simulations of electrical activity based on heart configurations that are based on at least some of subject heart characteristics such as scar locations, prior ablation locations and patterns, and heart orientation. If the s-lead ECG is indicative of an arrhythmia (e.g., atrial tachycardia), the simulations may be based on that type of arrhythmia. Each simulated heart configuration may assume a different source location of that type of arrhythmia. Depending on the computing resources available, the simulations may even be run in real time. The simulation "bootstrapping" techniques may be employed to speed up the running of the simulations. (See U.S. Pat. No. 10,860,754.)

Although described primarily as training based on simulated data, the ECG synthesis system may employ data collected from subjects. For example, the training data may include 12-lead ECGs. In such a case, the training data may include a subset of the leads labeled with one or more of the 12 leads. As another example, standard 12-lead ECGs and Holter monitor 3-lead ECGs may be collected simultaneously from subjects. In such a case, the training data may include the 3-lead ECG labeled with one or more of the 12 leads.

ECG Conversion

An ECG conversion system converts an ECG resulting from a nonstandard placement to one with a standard placement. A placement represents a mapping of an electrode identifier (e.g., RA or V2) to a location. A nonstandard placement ECG has at least one lead collected with an electrode in a nonstandard placement. A nonstandard placement can be determined in various ways. For example, using an ECG application of a smartphone (or other device), a subject can collect a subject nonstandard placement ECG and a placement image of the actual placement of electrodes (e.g., of a 3-lead patch) on the subject body. The ECG application can then send the placement image and the subject nonstandard placement ECG to the ECG conversion system (e.g., a cloud-based or a smartphone application). The ECG conversion system may determine whether the placement image represents a nonstandard placement. If so, the ECG conversion system converts the subject nonstandard placement ECG to a standard placement ECG. To assist in the conversion process, the ECG conversion system may maintain a mapping of users of the ECG application to user information such as type of ECG acquisition device, ECG history, number of leads, and so on.

The ECG conversion system may analyze the placement image to determine the actual location and the electrode identifier of each electrode. The actual locations may be determined, for example, based on distances relative to anatomical landmarks such as the clavicle, sternum, nipples, shoulders, navel, and so on, using triangulation. A 3-lead patch may include orientation markers that are visible when placing the 3-lead patch to assist in placement of the 3-lead patch in the standard orientation. The orientation marks may be used as landmarks when determining the nonstandard placement of electrodes of the patch. For example, the ECG conversion system may detect that the patch is oriented 10 degrees clockwise off its ideal orientation. The electrode identifiers may be determined based on a color marking on each electrode (e.g., white for RA, black for LA, and red for V1) or based on text marking on each electrode (e.g., RA, LA, and V1). The color identifier may be determined based on RGB values of a color image file, and the text identifier may be determined using character recognition.

The ECG application may estimate thorax characteristics of a subject using aspects of a body composition estimate system. For example, the subject's chest size, waist size, torso length, and so on may be estimated. The thorax characteristics may be derived based on laser imaging, detection, and ranging (LIDAR) scans, as described below. The ECG application may also input additional thorax characteristics such as body composition data. The body composition data may be received from a body composition system (described below) or a body composition scale. The body composition data may also be used when generating an ECG from simulated electrical activity based on body composition such as fat or muscle tissue that may affect conductivity and thus influence the voltage collected by an electrode.

The ECG conversion system may convert a nonstandard placement ECG using simulations (described above) of electrical activity of a heart. The ECG conversion system may generate, for each simulation and for each thorax configuration, an ECG conversion set with multiple simulated ECGs that are based on ECG specifications that are derived from the simulated electrical activity assuming that thorax configuration. An ECG conversion set may include a standard ECG and several nonstandard ECGs. For example, if there are five sets of thorax configurations and 10 nonstandard placements, the ECG conversion system generates five ECG conversion sets for each simulation with each ECG conversion set including 11 ECGs—one standard placement ECG and 10 nonstandard placement ECGs. The number of nonstandard placement ECGs can be increased to increase the chances that a standard placement ECG will accurately represent what would have been collected from the subject if the subject placement had been a standard placement.

The ECG conversion system identifies which of the placements of the ECG conversion sets (e.g., one standard placement and 10 nonstandard placements) is most similar to the subject placement. The ECG conversion system then identifies the ECG conversion set that has an ECG with the identified placement that is most similar to the subject ECG. The ECG conversion system outputs the standard ECG of the identified ECG conversion set as the subject standard ECG. If the subject placement is most similar to the standard placement, the subject ECG itself may be considered to be the subject standard (i.e., the subject ECG is not converted).

The ECG conversion system may alternatively perform the conversion on a lead-by-lead basis. Rather than an ECG conversion set being considered to include multiple-lead ECGs, the conversion set may be considered to have single-lead ECGs that are each associated with a placement. (A placement for a lead may specify the location of multiple electrodes.) For example, if there are 10 nonstandard placements for 12-lead ECGs, there may be 100 leads for nonstandard placements in an ECG conversion set. For each subject lead of the subject ECG, the ECG conversion system identifies which placement for a lead of the ECG conversion set is most similar to the subject placement for that subject lead. The ECG conversion system may then identify the ECG conversion set that contains leads for identified placements that are most similar to the leads of the subject ECG and select the standard ECG of that ECG conversion set as the subject standard ECG. In some embodiments, the subject ECG may have a number of leads that is more or less than the number of leads of the standard ECG of an ECG conversion set. In such a case, the ECG conversion system, as a way to synthesize leads, identifies the ECG conversion set based on that number of leads and selects the standard ECG of that ECG conversion set as the subject standard ECG.

The similarity between the actual placement and the placements of an ECG conversion set may be based on a similarity criterion. The similarity criterion may be based, for example, on the sum of the absolute value of the differences between the actual placement for the electrode(s) of each lead and the placement for the corresponding lead of an ECG conversion set. However, if the sum is greater than an overall threshold or if any difference is greater than a per-lead threshold, that placement may be considered to not satisfy the similarity criterion. The leads may be given different weights to account for the importance of each lead. The sum may be based on the differences of each placement for a lead multiplied by the weight for that lead. In such a case, the lead that is most important may be given a weight greater than the weights of the other leads.

ECG Machine Learning Techniques

In some embodiments, the ECG synthesis system may use various machine learning (ML) models to assist in the synthesis and conversion of ECGs. An ML model may input and output an entire ECG or an ECG portion such as a cycle. The ECG synthesis system may train an st-lead ML model for a t lead that inputs s leads (or one lead) and outputs a synthesized t lead. The ECG synthesis system trains the st-lead ML model using training data that includes, for each simulation, one or more simulated s leads labeled with a simulated t lead. To convert subject s leads to a synthesized t lead, the ECG synthesis system inputs the subject s leads to the trained st-lead ML model, which outputs the synthesized t lead.

In some embodiments, the st-lead ML model may be a convolutional neural network (CNN) that inputs an image, a recurrent neural network (RNN) that inputs a voltage-times series, or a neural network (NN) that inputs features (e.g., a QRS integral) derived from an image or voltage-time series for the subject s leads and outputs an image or voltage-time series of the synthesized t lead. In other embodiments, the st-lead ML model may have an autoencoder (AE) for each s lead that is used to encode a latent vector for that s lead. The latent vectors for the s leads are input to an NN that outputs an image or a voltage-time series of a synthesized t lead. Alternatively, rather than outputting an image or voltage-time series, the NN may output a latent vector representing the synthesized t lead. An AE may be trained using that t lead of each simulation. To train the NN, the encoder of that AE is used to generate for each simulation a latent vector for the simulated t lead. The training data is, for each simulation, the latent vectors for the s leads labeled as latent vectors for the simulated t lead generated using the encoder of the AEs. To generate a synthesized t lead, the latent vectors for the subject s leads are generated using the AEs. The latent vectors are input to the NN, which outputs a latent vector for the synthesized t lead. That latent vector is input to the decoder of the AE, which outputs the synthesized t lead.

The st-lead ML model may also be trained using additional training data such as data derived from heart characteristics and/or thorax characteristics. In such a case, for each simulation, s leads and the additional heart characteristics of the simulation and thorax characteristics used to generate the t lead are labeled with the corresponding t lead. The NN of such an st-lead ML model may input both the subject s leads and the subject heart characteristics and thorax characteristics and output a synthesized t lead. If some of the additional data (e.g., conduction velocity) of a subject is not known, a default value may be used, such as an average value from a population of subjects.

The ECG synthesis system may support the identification of which s leads should be used in generating a synthesized t lead. For example, lead I and lead V1 may be particularly effective s leads for synthesizing the t lead. The effective s leads could be identified by training ML models for a synthesized t lead, each of which inputs a different set of simulated s leads and outputs a synthesized t lead. The training data for each ML model may be, for each simulation, the set of simulated s leads labeled with the t lead. The effectiveness of an ML model can be determined by inputting, for each simulation of a collection of simulations, the s leads into the ML model, which outputs a synthesized t lead. The synthesized t leads can be compared to the simulated t leads to determine the effectiveness.

The ECG conversion system may train a conversion ML model to generate a converted ECG given a subject ECG and its placement. The conversion ML model may employ ML models that are similar to those described above for the synthesis ML model.

A neural network model has three major components: architecture, cost function, and search algorithm. The architecture defines the functional form relating the inputs to the outputs (in terms of network topology, unit connectivity, and activation functions). The search in weight space for a set of weights that minimizes the objective function is the training process. In one embodiment, the classification system may use a radial basis function (RBF) network and a standard gradient descent as the search technique.

A convolutional neural network (CNN) has multiple layers such as a convolutional layer, a rectified linear unit (ReLU) layer, a pooling layer, a fully connected (FC) layer, and so on. Some more complex CNNs may have multiple convolutional layers, ReLU layers, pooling layers, and FC layers.

A convolutional layer may include multiple filters (also referred to as kernels or activation functions). A filter inputs a convolutional window, for example, of an image, applies weights to each pixel of the convolutional window, and outputs an activation value for that convolutional window. For example, if the static image is 256 by 256 pixels, the convolutional window may be 8 by 8 pixels. The filter may apply a different weight to each of the 64 pixels in a convolutional window to generate the activation value, also referred to as a feature value. The convolutional layer may include, for each filter, a node (also referred to as a neuron) for each pixel of the image assuming a stride of one with appropriate padding. Each node outputs a feature value based on a set of weights for the filter that are learned.

The ReLU layer may have a node for each node of the convolutional layer that generates a feature value. The generated feature values form a ReLU feature map. The ReLU layer applies a filter to each feature value of a convolutional feature map to generate feature values for a ReLU feature map. For example, a filter such as max(0, activation value) may be used to ensure that the feature values of the ReLU feature map are not negative.

The pooling layer may be used to reduce the size of the ReLU feature map by downsampling the ReLU feature map to form a pooling feature map. The pooling layer includes a pooling function that inputs a group of feature values of the ReLU feature map and outputs a feature value.

The FC layer includes some number of nodes that are each connected to every feature value of the pooling feature maps.

As described above, the ML models may input different modalities such as images, heart characteristics, thorax characteristics, and placements. The ML models may employ a multimodal ML approach, referred to as "early fusion," in which data of the different modalities is combined at the input stage and an ML model is then trained on the multimodal data. The training data for these modalities includes a collection of sets of an image, heart characteristics, thorax characteristics, and placements and labels. The data may be used in its original form or preprocessed, for example, to reduce its dimensionality by compressing the data into byte arrays. Also, the resolutions of the images may be reduced. The concatenated bytes may be then processed by a cross-attention mechanism to condense the concatenated bytes into a vector of a fixed size. The vectors are then used to train an ML model.

In some embodiments, the ECG synthesis system, the ECG conversion system, and the ECG machine learning techniques may divide an ECG into ECG portions such as cycles (e.g., beats). To process the portions separately, the ECG synthesis system and the ECG conversion system may first calibrate the simulated ECGs based on heart configurations, thorax configurations, and/or placements that are similar to those of the subject. The systems may then process each subject ECG portion to identify a simulated ECG portion of the calibrated simulated ECGs that is similar to that subject ECG portion. The collection of the similar subject ECG portions represents a synthesized ECG and/or a converted ECG. The ML model may be trained using training data that includes ECG portions that are each labeled with a synthesized ECG portion and/or a converted ECG portion. An electrogram (e.g., ECG) may have any number of leads, such as one lead collected by a smartwatch or 12 leads collected by a medical-grade ECG acquisition device.

Body Composition Estimate System

A body composition estimate (BCE) system is provided that estimates body composition based on a full or partial body scan generated using a laser imaging, detection, and ranging (LIDAR) device (e.g., in a smartphone, smartwatch, tablet) and/or using various machine learning techniques.

Body composition specifies the percentage of fat, bone, water, and muscle in a body. The BCE system may estimate the amount of fat in a body as a function of body density. Body fat Br may be estimated by the following formula:

$$B_f = ((4.950/B_d) - 4.5) * 100$$

where $B_d$ is body density. (Siri, W., "Body composition from fluid spaces and density: analysis of methods," 1956.) $B_d$ is represented by the following equation:

$$B_d = B_m/B_v$$

where $B_m$ is body mass in air and $B_v$ is body volume. $B_v$ may be represented by the equation:

$$B_v = ((B_m - B_{mw})/W_d) - R_v$$

where $B_{mw}$ is body mass in water, $W_d$ is the density of water, and $R_v$ is residual volume. $R_v$ represents the empty space in the body (e.g., in the lungs). $R_v$ can be measured based on the volume of air that is exhaled.

The accurate measurement of $B_{mw}$ and $R_v$ requires a specialized setting that is both expensive and inconvenient for most people. $B_v$ may be determined using "hydrostatic weighing." Hydrostatic weighing is performed based on the volume of displaced water when the body is immersed in water. However, the $R_v$ may be estimated by the following formula:

$$R_v = 1.310*H + .022*A - 1.232 \text{ (Men)}$$

$$R_v = 1.812*H + .016*A - 2.003 \text{ (Women)}$$

where H is height and A is age. (Quanjer, P., "Standardized lung function testing," 1983).

Unfortunately, the calculation of $B_{mw}$ typically requires hydrostatic weighing. The BCE system, however, provides an estimate of $B_v$ without hydrostatic weighing. To estimate $B_v$, the BCE system may employ LIDAR technology. LIDAR technology determines distance to an object based on the time-of-flight of light. The time-of-flight is a measure of the time between when the laser signal is transmitted $T_t$ and when the return signal that is reflected from an object is received $T_r$. The distance D to the reflecting object is represented by the following equation:

$$D = (T_r - T_t)/(2*c)$$

where c is the speed of light.

Fortunately, portable devices (e.g., smartphones) may include a LIDAR device that includes a transmitter and a receiver. The BCE system uses the LIDAR device to estimate $B_v$. To estimate $B_v$, a BCE application of the BCE system executing on a smartphone directs a subject to stand (preferably naked) in front of the smartphone and collects a body scan using the LIDAR device. To collect the body scan, the LIDAR is used to measure the distance to the body at various locations. The distance can be used, for example, to determine the width of the body at the navel based on a front view and a side view of the body. If the subject stands a few feet away from a background (e.g., a wall), the outline of the body can be determined based on the shorter time-of-flight of light reflected by the body. The subject may extend their arms horizontally to include the arms in the outline. The BCE system determines the outline from different views, such as a frontal view, a back view, and a side view.

The BCE system may perform a series of horizontal scans in vertical scan increments from the top of the head to the feet. If the subject has a height of 1.75 meters and the vertical scan increment is 2.5 centimeters, then the BCE system performs 70 horizontal scans. The BCE system may employ a scan width of 1.0 meters and determine a time-of-flight at horizontal scan increments. If a subject has a width of 0.5 meters at a horizontal scan and the horizontal scan increment is 1.0 centimeters, the BCE system collects 50 time-of-flights for light reflected from the body and determines 50 distances to the body.

A subject may be offset slightly from one view to the next to the left or right or closer to or farther from the LIDAR device. This may occur because the subject may not rotate around the same vertical axis. The BCE system may use the subject's height to calibrate the scans of the views to determine the offsets. The offsets may be calculated based on triangulation given the height, distance to the background (e.g., a wall) relative to the body, and so on. The BCE system may select an initial reference frame based on the first view. The BCE system translates the distances of each view given the offset of the view to distances in the initial reference frame.

The BCE system calculates a 3D outline of the body based on a 2D outline created for each vertical scan increment based on the distances to the body, which are determined from the views. The 2D outline can be considered to represent a horizontal body slice. The BCE system may generate a 2D outline for each arm and leg and calculate a volume for each. Thus, the body volume would be the sum of the non-limb volume (i.e., torso, neck, and head) plus the limb volume (i.e., arms and legs). Given the body slices (limb and non-limb), the BCE system may calculate the incremental body volume for each slice by, for example, calculating the volume assuming a height of 2.5 cm. The BCE then sums the incremental body volume to give an estimate of the body volume.

The BCE system supports a body scan taken by a subject holding the LIDAR device, such as one that is in a smartphone. To perform the scan, a subject holds the smartphone at various positions relative to the body to scan a portion of the body from each position. For example, the positions may be in front and on the side of the head, chest, abdominal region, pelvic region, an upper and lower leg, and an upper arm and a forearm. The positions may also include in back of the gluteus area. Depending on the spread of the LIDAR signals, the scan may need to include many more positions. In such a case, the body scan may be of only half of the body, such as the left front and left side. The body volume may be estimated as twice the volume of the half. Also, the BCE system may employ a mirror image of the left side as a representation of the right side. The BCE system "stitches" the scans to together to form a full body scan.

In some cases, a body scan may have portions of the body missing, referred to as a gap. For example, a subject may think they are scanning the entire thorax but are only scanning the left 75% of the thorax due to the angle of the LIDAR device held in the right hand. To account for such a gap, the BCE system may employ a gap machine learning (ML) model that fills in the gaps. The gap ML model (e.g., a convolutional neural network) may be trained with training data that includes gap images labeled with non-gap images. The training data may be generated from a collection of non-gap images generating gap images (e.g., automatically) from each non-gap image by removing various portions. A gap image is labeled with the non-gap image from which it was derived. A similar approach may be used to fill in gaps in a LIDAR scan. To fill in a LIDAR scan, another gap ML model may be trained using training data that includes gap LIDAR scans labeled with the corresponding non-gap LIDAR scans. The training data may be generated from a collection of simulated or actual non-gap LIDAR scans by generating gap LIDAR scans (e.g., automatically) from the non-gap LIDAR scans by removing various portions. A gap LIDAR scan is labeled with the non-gap LIDAR scan from which it was derived.

The BCE system may provide instructions (e.g., visual, audio, or haptic) to guide the subject in performing a scan. For example, the instructions may indicate to hold the smartphone in front of a body area and direct the subject to hold the smartphone at the most desirable position, such as instructions to move the smartphone to the left, up, or closer or to adjust its tilt. The instructions may be generated based on a determination of the portion of the body that would be covered by a scan given the current location of phone. For example, if the scan would leave a gap, an instruction may be to hold the smartphone farther away or to the left. When the scan of a region is complete, the BCE system may inform the subject that the scan is complete and instruct the subject to move the LIDAR device to the next position. The BCE system may also display an image of the body (e.g., collected by the smartphone), which may indicate the portion within the beam spread of the LIDAR device.

In some cases, a subject may not be able to take a body scan or collect a body image when naked, for example, because of privacy concerns. For example, a woman may want to wear a bra and underwear, and a man may want to wear pants. Given a full body scan of such a subject, the BCE system may receive from the subject an indication of the clothing being worn or may infer what clothing is being worn. To infer the clothing being worn, the ECG system may train a clothing ML model using training data that includes body images (collected or simulated) labeled with the type of clothing being worn, if any. When presented with a body image, the BCE system inputs the body image to the clothing ML model to determine the clothing being worn. Based on the clothing being worn, the BCE system may estimate body volume by estimating the outline of the body portion that is covered, for example, based on the LIDAR measurements of the covered portions.

The BCE system may alternatively employ ML techniques to estimate a target body measurement, such as body volume or to body density. The BCE system may train a BCE ML model using training data that includes, for each body, body images from one or more views, the body height, and the target body measurement. (The body images may be of people who are naked or partially clothed.) Once trained, the BCE ML model is applied to body images of a subject and the subject's height to provide an estimate of the target body measurement for the subject. An advantage of the BCE ML model is that the target body measurement can be estimated for any subject with an image capture device (e.g., camera or smartphone) without the need for a LIDAR sensor.

The training data may be data collected from various sources. The training data may include hydrostatic data that includes body volume along with body images collected by a hydrostatic weighing facility. The training data may include avatar data collected by a body shape simulator that generates 3D representations (e.g., a 3D mesh) of bodies with varied sizes and shapes and calculates their volumes. From a 3D representation, "skin" may be superimposed on the 3D representation to generate an avatar and render images of the avatar from different views. The training data may include LIDAR data such as body composition determined using a LIDAR device as described above and body images collected during a body scan. Rather than collecting body images, the body images can be created from an avatar based on a 3D representation of the body derived from a LIDAR scan, effectively bootstrapping the BCE ML model using the data collected by the BCE system.

The BCE ML model may be based on a convolutional neural network (CNN). Various CNN architectures may be used. One architecture may employ a single CNN that inputs, for example, a frontal view, a side view, and a height and outputs the body volume. Another architecture may employ a CNN autoencoder for each view to generate latent features for each view. The latent features along with other features (e.g., height, age, sex, ethnicity, body mass) may be input to a neural network (NN), which outputs a body measurement (e.g., body volume, body density, or body composition).

The BCE system may also estimate body composition based on data collected by a body composition scale. A body composition scale may employ a bioelectrical impedance analysis (BIA) based on an electric current sent through a body when standing on the body composition scale to determine body composition. The body composition data may relate to body fat, muscle mass, bone density, body water percentage, and so on. However, because of the limitations and assumptions of a typical body composition scale, the resulting body composition may not be particularly accurate.

To correct for the lack of accuracy in such body composition data, the BCE system may employ a body composition correction (BCC) ML model that inputs body composition scale data and outputs a corrected body composition. The training data may be collected using a LIDAR device as described above and corresponding scale-based body composition data. Some of the people who employ a LIDAR device to determine body composition may also have a body composition scale. In addition to collecting the scans, the BCE system may also collect scale-based body composition data. If the LIDAR device is a smartphone, the smartphone can connect to the body composition scale using a wireless (e.g., WiFi or Bluetooth) connection and receive the scale-based body composition data. The BCC ML model may input scale-based body composition data along with other data (e.g., height and weight) and output a corrected body composition. A separate BCC ML model may be trained for different scale models of body composition scales (e.g., by different manufacturers) to make a correction that is appropriate for each scale model. The BCE system may also employ scale-based body composition data as additional information to augment the calculating of LIDAR-based body composition, resulting in a LIDAR/scale-based body composition.

The BCE system may also maintain, for each subject, LIDAR images, body images, time of capture, body composition, and so on. The BCE system can generate and display a graphic that shows the evolution of the body composition over time. For example, the BCE system may generate a video that animates the change in body composition from body image to body image, filling in frames between acquired body images with interpolated images. For example, if the animation is to include a frame for each day and body images are taken a week apart, the GCE system may generate each interpolated body image by incrementally adjusting each body dimension (e.g., waist width) by one-seventh of the weekly difference. The change in body composition can also be illustrated using an avatar based on the 3D representation of the body. The BCE system may also provide various graphics such as graphs plotting fat percentage, muscle percentage, and weight over time.

The BCE system may also estimate body composition based on various manual measurements of physical features of the subject such as abdominal circumference, thorax circumference, hip circumference, heights of different body regions (e.g., thorax), and so on. The BCE system may employ an ML model that is trained using training data that includes the measurements labeled with body composition. The training data may be data of medical databases, data generated from the LIDAR scans and calculations of body composition, and so on. These measurements may also be used in combination with a LIDAR scan to augment the training data for an ML model to determine body composition.

The BCE system may also interface with various personal devices (e.g., smartphones) and electronic health record systems (e.g., of a hospital) that track, collect, and/or store a subject's characteristics such as age, sex, weight, heart rate, and so on over time. By collecting the data from these devices, the BCE system can use the data to further augment the data used in the techniques described above.

FIG. 1 is a flow diagram that illustrates components of an ECG processing system in some embodiments. The ECG processing system 100 includes a generate ECG conversion set component 101, a run simulation component 102, a determine subject placement component 103, a synthesize ECG component 104, a convert ECG component 105, an identify similar thorax configuration component 106, an identify similar heart configurations component 107, and an identify similar ECG specification component 108. The generate ECG conversion set component generates ECG conversion sets for combinations of heart configurations, thorax configurations, and ECG specifications. The generate ECG conversion set component invokes the run simulation component for each heart configuration. The run simulation component runs a simulation of electrical activity of a heart having a specified heart configuration. The generate ECG conversion set component then generates an ECG conversion set for each combination of a simulation and thorax configuration that includes an ECG for each ECG specification.

The determine subject placement component determines the placement of electrodes on the body of a subject based on a subject image. The synthesize ECG component synthesizes ECGs based on a subject ECG. The convert ECG component converts an ECG to an ECG having a different placement. The identify similar thorax configuration component identifies a thorax configuration used to generate the ECGs that are similar to a subject thorax configuration. The identify similar heart configurations component identifies subject heart configurations that are similar to the subject heart configuration. The identify similar ECG specification component identifies an ECG specification that is similar to the subject placement of electrodes and mapping of the electrodes to leads of the subject ECG.

The ECG processing system may interface with a simulation data store 110, an electronic health records (EHR) system 120, an ablation planning system 130, a smartphone 140, and a medical-grade ECG acquisition device 150. The simulation data store stores, for each heart configuration, a mapping of that heart configuration to the simulated electrical activity based on that heart configuration and, for each thorax configuration and placement, to the ECG specification generated based on that thorax configuration from that simulated electrical activity and that placement. The EHR system stores medical records of the subject. The ablation planning system receives a synthesized ECG and/or converted ECG from the ECG processing system and may identify an arrhythmia type, an arrhythmia location, and an ablation pattern to support an ablation to treat the arrhythmia of the subject. The smartphone collects a subject ECG and a subject placement image and provides them to the ECG processing system. The ECG processing system may provide a synthesized ECG and/or a converted ECG that is based on the received subject ECG and the subject placement image to the smartphone for display to the subject. The ECG processing system may receive an ECG from the medical-grade ECG device during an ablation procedure and provide a synthesized ECG and/or converted ECG to the ablation planning system.

The computing systems (e.g., network nodes or collections of network nodes) on which the BCE system, the ECG synthesis system, the ECG conversion system, and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, distributed systems, cloud-based computing systems, client computing systems that interact with cloud-based computing systems, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the described systems. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extension (SGX)) for generating and securely storing keys and for encrypting and decrypting data using the keys and for securely executing all or some of the computer-executable instructions of the system. Some of the data sent by and received by the systems may be encrypted, for example, to preserve personal privacy (e.g., to comply with government regulations, such as the European General Data Protection Regulation (GDPR) or the Health Insurance Portability and Accountability Act (HIPAA) of the United States). The systems may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each execute computer-executable instructions of the systems. A client-side computing system, such as a smartphone, may send data to and receive data from one or more servers of the cloud-based computing systems of one or more cloud data centers. For example, a client-side computing system may send a request to a cloud-based computing system to perform tasks such as running a subject-specific simulation of electrical activity of a heart or training a subject-specific machine learning model. A cloud-based computing system may respond to the request by sending to the client-side computing system data derived from performing the task, such as a synthesized ECG and/or a converted ECG. The servers may perform computationally expensive tasks in advance of processing by a client-side computing system, such as training a machine learning model, or in response to data received from a client-side computing system. A client-side computing system may provide a user experience (e.g., user interface) to a user of the systems. The user experience may originate from a client computing device or a server computing device. For example, a client computing device may generate a graphic representing the ECG received from the ECG processing system. Alternatively, a cloud-based computing system may generate the graphic (e.g., in a HyperText Markup Language (HTML) format or an Extensible Markup Language (XML) format) and provide it to the client-side computing system for display. A client-side computing system (e.g., ablation planning device) may also send data to and receive data from various medical devices, such as an arrhythmia mapping system, an EHR system, and so on. The data received from the medical devices may include an ECG, actual ablation characteristics (e.g., ablation location and ablation pattern), and so on. The term "cloud-based computing system" may encompass computing systems of a public cloud data center provided by a cloud provider (e.g., Azure provided by Microsoft Corporation) or computing systems of a private server farm (e.g., operated by the provider of the systems).

Figure 2:
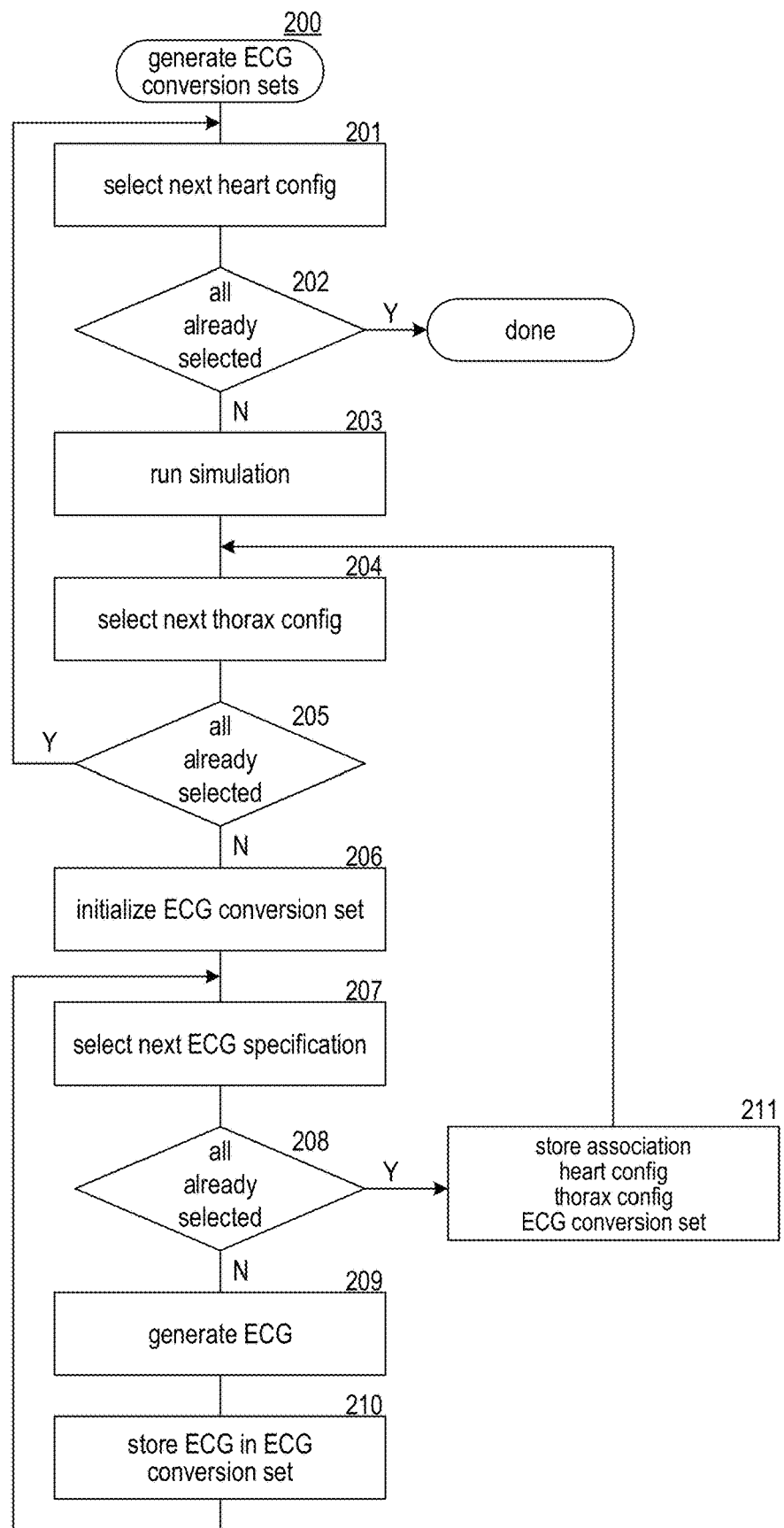
FIG. 2 is a flow diagram that illustrates the processing of a generate ECG conversion of the ECG processing system in some embodiments.

FIG. 2 is a flow diagram that illustrates the processing of a generate ECG conversion of the ECG processing system in some embodiments. The generate ECG conversion sets component 200 is invoked to generate ECG conversion sets based on simulated electrical activity. In block 201, the component selects the next heart configuration. In decision block 202, if all the heart configurations have already been selected, then the component completes, else the component continues at block 203. In block 203, the component runs a simulation assuming the selected heart configuration to generate simulated electrical activity of the heart. In block 204, the component selects the next thorax configuration. In decision block 205, if all the thorax configurations have already been selected, then the component loops to block 201 to select the next heart configuration, else the component continues at block 206. In block 206, the component initializes an ECG conversion set. In block 207, the component selects the next ECG specification. In decision block 208, if all the ECG specifications have already been selected, then the component continues at block 211, else the component continues at block 209. In block 209, the component generates an ECG based on the selected simulation, thorax configuration, and ECG specification. In block 210, the component stores the ECG in the ECG conversion set and then loops to block 207 to select the next ECG specification. In block 211, the component stores an association between the selected heart configuration, the selected thorax configuration, and the ECG conversion set and loops to block 204 to select the next thorax configuration.

Figure 3:
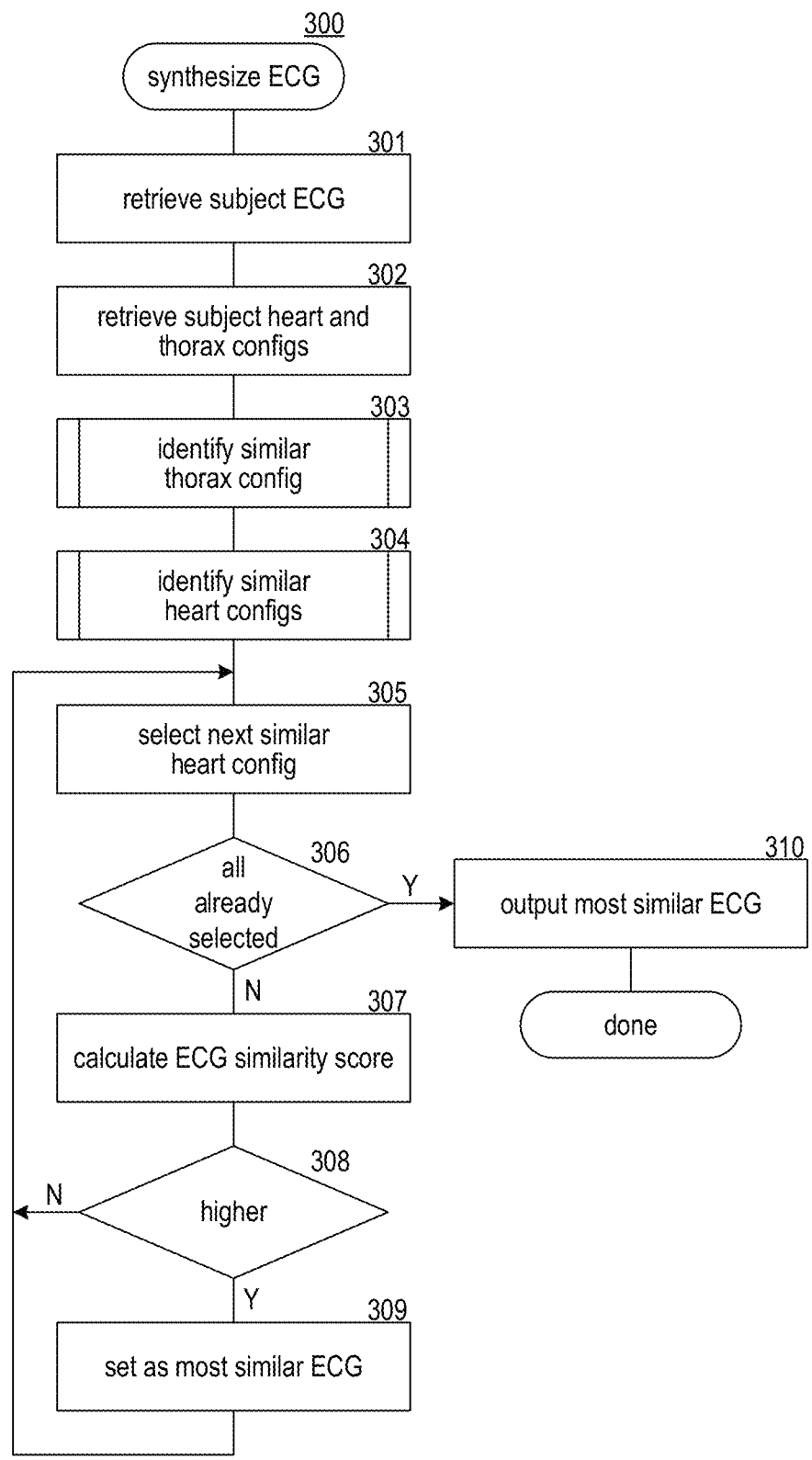
FIG. 3 is a flow diagram that illustrates the processing of a synthesize ECG component of the ECG processing system in some embodiments.

FIG. 3 is a flow diagram that illustrates the processing of a synthesize ECG component of the ECG processing system in some embodiments. The synthesize ECG system 300 generates a synthesized ECG given a subject ECG based on both heart configuration calibration and thorax configuration calibration. In block 301, the component retrieves a subject ECG. In block 302, the component retrieves the subject heart configuration and the subject thorax configuration. In block 303, the component invokes the identify similar thorax configuration component to calibrate based on the most similar thorax configuration. In block 304, the component invokes the identify similar heart configurations component to calibrate based on the most similar heart configurations. In block 305, the component selects the next similar heart configuration. In decision block 306, if all the similar heart configurations have already been selected, then the component continues at block 310, else the component continues at block 307. In block 307, the component calculates an ECG similarity score between the subject ECG and the simulated ECG generated based on the simulated electrical activity of the simulation that was based on the selected heart configuration. In decision block 308, if the ECG similarity score is greater than the highest ECG similarity score previously calculated, then the component continues at block 309, else the component loops to block 305 to select the next similar heart configuration. In block 309, the component sets that simulated ECG as the most similar ECG and then loops to block 305 to select the next similar heart configuration. In block 310, the component outputs the most similar ECG as the synthesized ECG and then completes.

Figure 4:
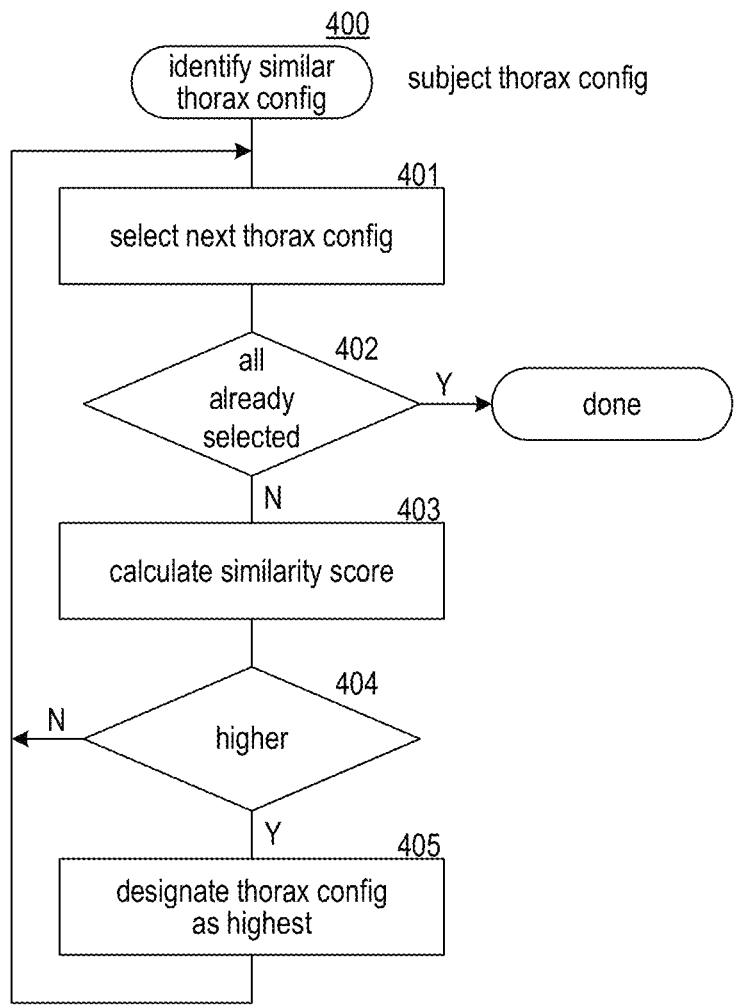
FIG. 4 is a flow diagram that illustrates processing of an identify similar thorax configuration component of the ECG processing system in some embodiments.

FIG. 4 is a flow diagram that illustrates processing of an identify similar thorax configuration component of the ECG processing system in some embodiments. The identify similar thorax configuration component 400 inputs a subject thorax configuration and identifies the most similar simulated thorax configuration used to generate simulated ECGs from the simulated electrical activity. Alternatively, the component may identify multiple similar thorax configurations. In such a case, the ECG synthesis system and the ECG conversion system may identify, from the simulated ECGs generated for each combination of a similar heart configuration and a similar thorax configuration, a simulated ECG that is similar to the subject ECG. In block 401, the component selects the next thorax configuration. In decision block 402, if all the thorax configurations have already been selected, then the component completes, returning an indication of the most similar thorax configuration, else the component continues at block 403. In block 403, the component calculates a thorax similarity score between the selected thorax configuration and the subject thorax configuration. In decision block 404, if the thorax similarity score is higher than all previously calculated thorax similarity scores, then the component continues at block 405, else the component loops to block 401 to select the next thorax configuration. In block 405, the component designates the selected thorax configuration as the most similar thorax configuration and loops to block 401 to select the next thorax configuration.

Figure 5:
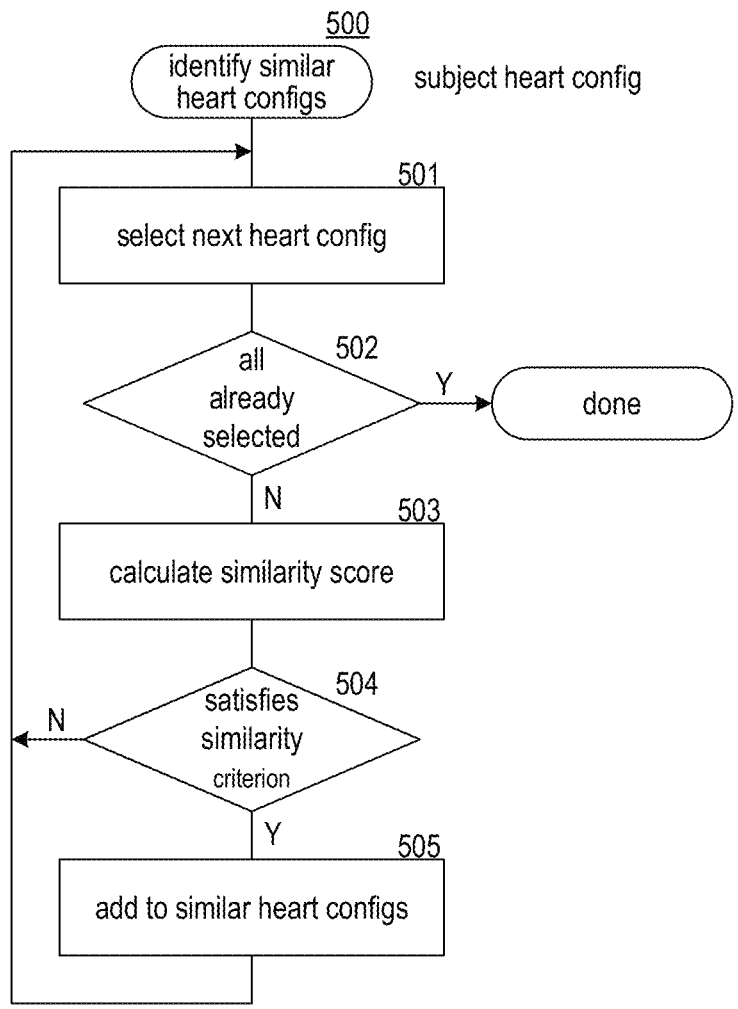
FIG. 5 is a flow diagram that illustrates the processing of an identify similar heart configurations component of the ECG processing system in some embodiments.

FIG. 5 is a flow diagram that illustrates the processing of an identify similar heart configurations component of the ECG processing system in some embodiments. The identify similar heart configurations component 500 is invoked to identify heart configurations that are similar to a subject heart configuration. In block 501, the component selects the next heart configuration. In decision block 502, if all the heart configurations have already been selected, then the component completes, returning an indication of the similar heart configurations, else the component continues at block 503. In block 503, the component calculates a heart similarity score between the selected heart configuration and the subject heart configuration. In decision block 504, if the heart similarity score satisfies a similarity criterion (e.g., above a threshold value), then the component continues at block 505, else the component loops to block 501 to select the next heart configuration. Rather than employing a similarity criterion, the component may select some number (e.g., 20) of the most similar heart configurations. In block 505, the component adds the selected heart configuration to a set of similar heart configurations and then loops to block 501 to select the next heart configuration.

Figure 6:
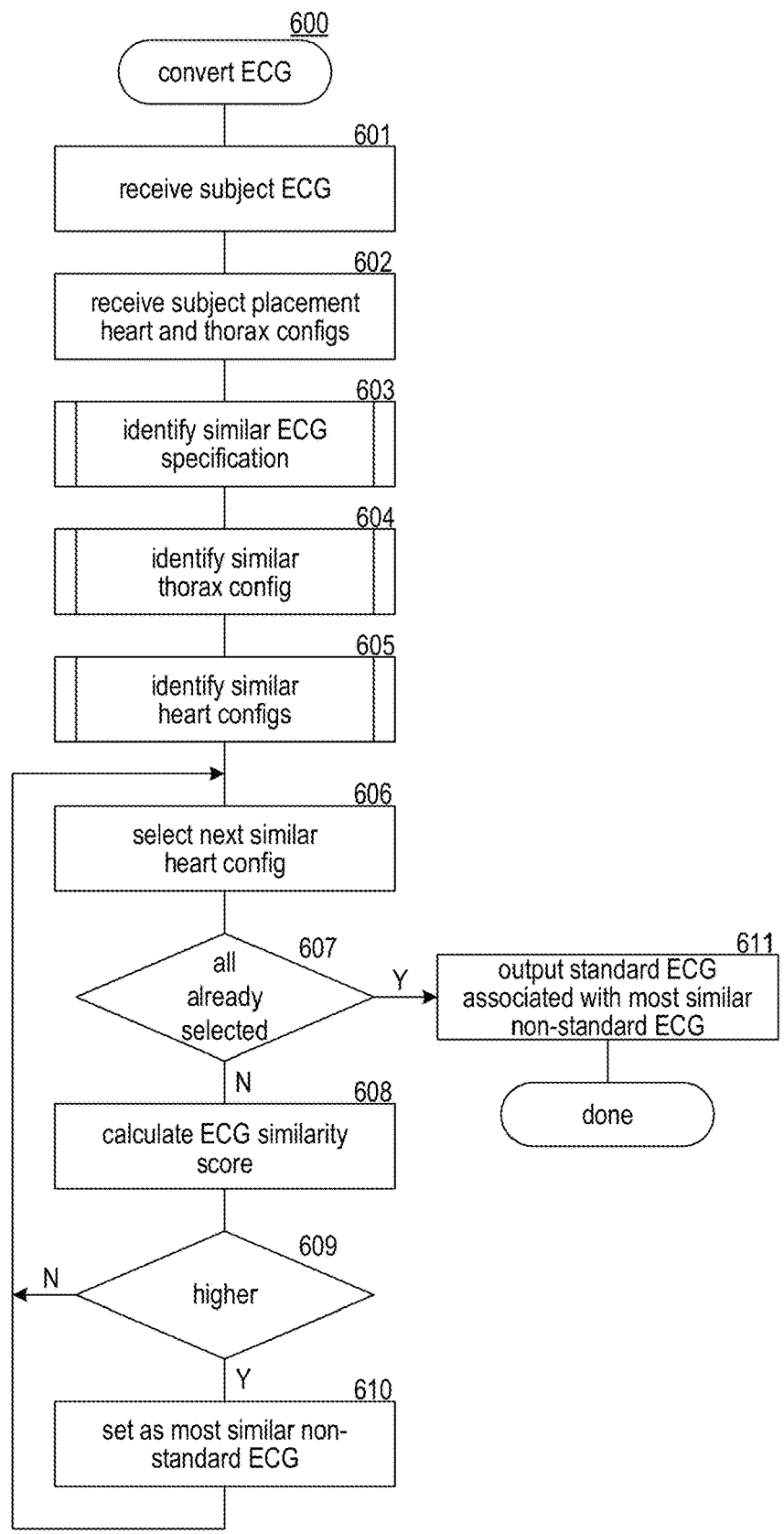
FIG. 6 is a flow diagram that illustrates the processing of a convert ECG component of the ECG processing system in some embodiments.

FIG. 6 is a flow diagram that illustrates the processing of a convert ECG component of the ECG processing system in some embodiments. The convert ECG component converts a subject ECG to a standard ECG. In block 601, the component receives the subject ECG. In block 602, the component receives the subject placement, subject heart configuration, and subject thorax configuration. In block 603, the component invokes an identify similar ECG specification component to identify the most similar ECG specification used when generating the ECG conversion sets. In block 604, the component invokes the identify similar thorax configuration component to identify the most similar thorax configuration used to generate the ECG conversion sets. In block 605, the component invokes the identify similar heart configurations component to identify heart configurations used in the simulations that are similar to the subject heart configuration. In block 606, the component selects the next similar heart configuration. In decision block 607, if all the similar heart configurations have already been selected, then the component continues at block 611, else the component continues at block 608. In block 608, the component calculates an ECG similarity score between the ECG generated from the simulated electrical activity of the simulation based on the selected heart configuration assuming the similar thorax configuration and the similar placement. In decision block 609, if the calculated ECG similarity score is higher than any similarity score calculated so far, then the component continues at block 610, else the component loops to block 606 to select the next similar heart configuration. In block 610, the component sets that calculated ECG similarity score as the most similar nonstandard ECG and loops to block 606 to select the next similar heart configuration. In block 611, the component outputs the standard ECG associated with the most similar nonstandard ECG as corresponding to the subject standard ECG and completes.

Figure 7:
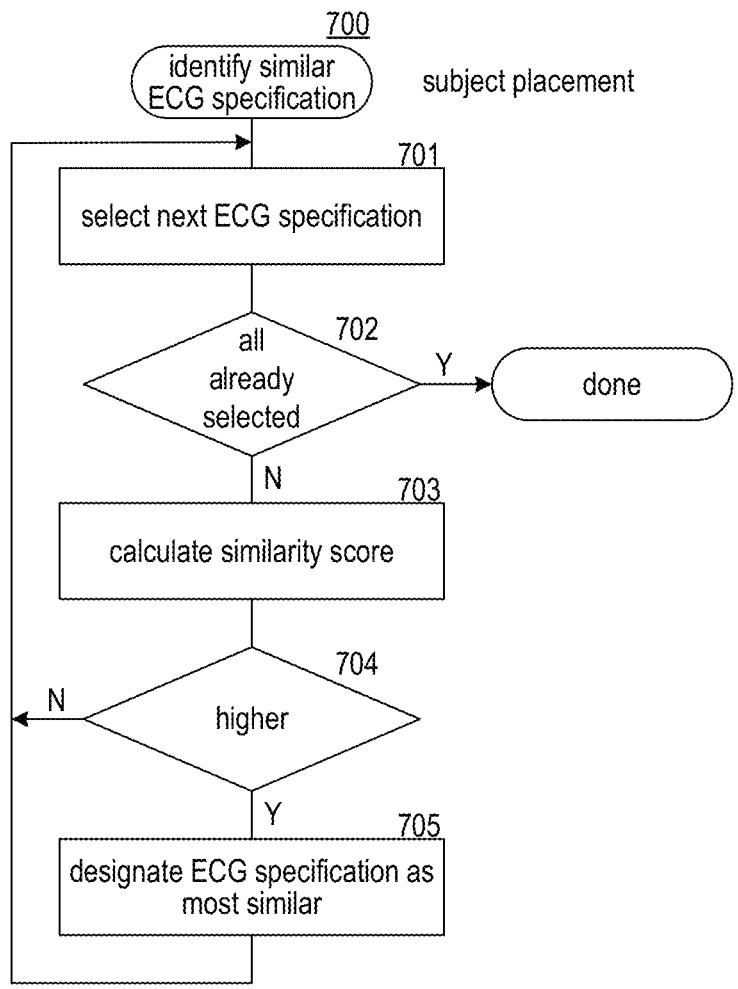
FIG. 7 is a flow diagram that illustrates the processing of an identify similar ECG specification component of the ECG processing system in some embodiments.

FIG. 7 is a flow diagram that illustrates the processing of an identify similar ECG specification component of the ECG processing system in some embodiments. The identify similar ECG specification component 700 is invoked to determine the ECG specification that is most similar to the subject ECG specification. In block 701, the component selects the next ECG specification used to generate the ECG conversion sets. In decision block 702, if all the ECG specifications have already been selected, then the component completes, indicating the most similar ECG specification, else the component continues at block 703. In block 703, the component calculates a similarity score between the selected ECG specification and the subject ECG specification. In block 704, if that similarity score is higher than the highest similarity score that has been calculated thus far, then the component loops to block 701 to select the next ECG specification, else the component continues at block 705. In block 705, the component designates the selected ECG specification as having the highest similarity score and then loops to block 701 to select the next ECG specification.

Figure 8:
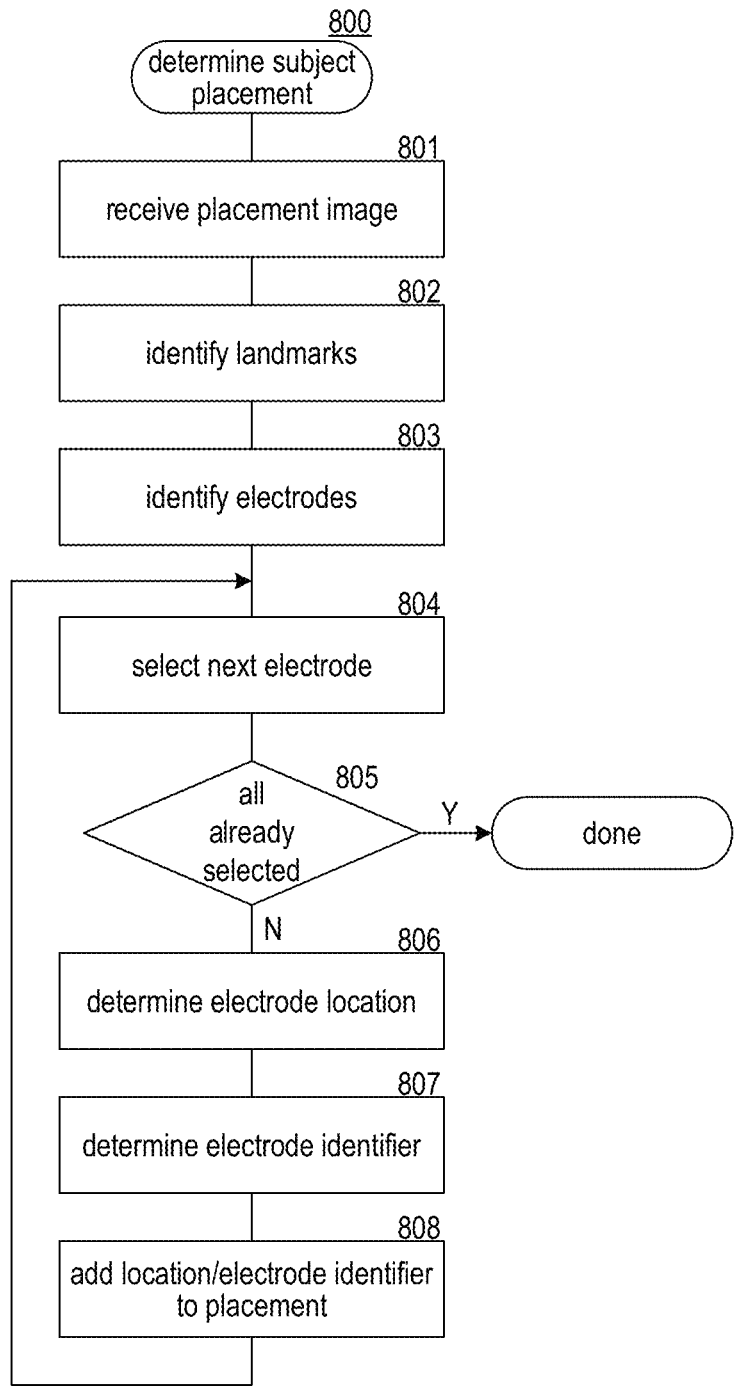
FIG. 8 is a flow diagram that illustrates the processing of a determine subject placement component of the ECG processing system in some embodiments.

FIG. 8 is a flow diagram that illustrates the processing of a determine subject placement component of the ECG processing system in some embodiments. The determine subject placement component 800 determines the placement of electrodes on the body of a subject based on a placement image of the body. In block 801, the component receives the placement image. In block 802, the component identifies landmarks within the placement image. In block 803, the component identifies electrodes within the placement image. In block 804, the component selects the next electrode. In decision block 805, if all the electrodes have already been selected, then the component completes, else the component continues at block 806. In block 806, the component determines the location of the electrode. In block 807, the component determines the electrode identifier of the electrode. In block 808, the component adds to the subject placement a mapping of the electrode identifier to the location and then loops to block 804 to select the next electrode.

The following paragraphs describe various aspects of the ECG processing system and the BCE system. Implementations of these systems may employ any combination or sub-combination of the aspects and may employ additional aspects. The processing of the aspects may be performed by one or more computing systems with one or more processors that execute computer-executable instructions that implement the aspects and that are stored on one or more computer-readable storage mediums.

In some aspects, the techniques described herein relate to a method performed by one or more computing systems for converting a subject electrogram based on a subject placement of electrodes to a converted subject electrogram that is based on a target placement of electrodes, the method including receiving the subject electrogram and the subject placement of electrodes; accessing a collection of simulated source electrograms and simulated target electrograms, each simulated source electrogram based on a source placement of electrodes and each simulated target cardiogram based on a target placement of electrodes, each simulated target electrogram associated with, for each of a plurality of source placements, a simulated source electrogram; identifying a source placement based on similarity to the subject placement; identifying a simulated source electrogram associated with the identified source placement based on similarity to the subject electrogram; designating the simulated target electrogram that is associated with the identified simulated source electrogram as the converted subject electrogram; and outputting the converted subject electrogram. In some aspects, the techniques described herein relate to a method wherein the electrograms are cardiograms. In some aspects, the techniques described herein relate to a method wherein the electrograms are vectorcardiograms. In some aspects, the techniques described herein relate to a method wherein an electrogram represents electrical activity of an organ in a body. In some aspects, the techniques described herein relate to a method wherein each simulated source electrogram is a nonstandard cardiogram based on a nonstandard placement of electrodes and each simulated target electrogram is a standard cardiogram based on a standard placement of electrodes. In some aspects, the techniques described herein relate to a method wherein each simulated target electrogram and the associated simulated source electrograms are generated based on a simulation of electrical activity of a heart based on a heart configuration of a plurality of heart configurations. In some aspects, the techniques described herein relate to a method further including, prior to identifying a simulated source electrogram, calibrating the collection based on similarity of the plurality of heart configurations to a subject heart configuration. In some aspects, the techniques described herein relate to a method wherein each simulated target electrogram and the associated simulated source electrograms are generated based on a thorax configuration of a plurality of thorax configurations. In some aspects, the techniques described herein relate to a method further including, prior to identifying a simulated source electrogram, calibrating the collection based on similarity of the thorax configuration to a subject thorax configuration. In some aspects, the techniques described herein relate to a method wherein the subject placement of electrodes is represented by an image of the electrodes after being placed. In some aspects, the techniques described herein relate to a method wherein an electrogram acquisition device collects the subject electrogram and sends the subject electrogram to a smartphone and the smartphone collects a subject image of the subject placement of electrodes and sends the subject electrogram and the subject image to the one or more computing systems.

In some aspects, the techniques described herein relate to one or more computing systems for synthesizing a synthesized cardiogram based on a subject cardiogram of a subject, the one or more computing systems including one or more computer-readable storage mediums that store computer-executable instructions for controlling the one or more computing systems to access a collection of mappings that each maps a simulated source cardiogram to an associated simulated target cardiogram, the simulated source cardiograms and the simulated target cardiograms being generated based on simulations of electrical activity of a heart; access a subject cardiogram; identify a simulated source cardiogram based on similarity to the subject cardiogram; designate the simulated target cardiogram associated with the identified simulated source cardiogram as a synthesized subject cardiogram; and output the synthesized subject cardiogram; and one or more processors for controlling the one or more computing systems to execute one or more of the computer-executable instructions. In some aspects, the techniques described herein relate to one or more computing systems wherein a simulated source cardiogram has three leads and a simulated target cardiogram has 12 leads. In some aspects, the techniques described herein relate to one or more computing systems wherein a simulated source cardiogram has multiple leads and a simulated target cardiogram has one lead. In some aspects, the techniques described herein relate to one or more computing systems wherein each simulated source cardiogram and the associated simulated target cardiogram are associated with a heart configuration of a plurality of heart configurations. In some aspects, the techniques described herein relate to one or more computing systems wherein the computer-executable instructions include instructions to, prior to identifying a simulated target cardiogram, calibrate the collection based on similarity of a subject heart configuration to the plurality of heart configurations. In some aspects, the techniques described herein relate to one or more computing systems wherein each simulated source cardiogram and the associated simulated target cardiogram are associated with a thorax configuration of a plurality of thorax configurations. In some aspects, the techniques described herein relate to one or more computing systems wherein the computer-executable instructions include instructions to, prior to identifying a simulated source cardiogram, calibrate the collection based on similarity of a subject thorax configuration to the plurality of thorax configurations. In some aspects, the techniques described herein relate to one or more computing systems wherein the subject cardiogram is associated with a subject placement of electrodes, a simulated source cardiogram is associated with a source placement of electrodes of a plurality of source placements of electrodes, and the associated simulated target cardiogram is associated with a target placement of electrodes and wherein the identification of a simulated source cardiogram is further based on similarity of the subject placement to a source placement. In some aspects, the techniques described herein relate to one or more computing systems wherein a cardiogram acquisition device collects the subject cardiogram and sends the subject cardiogram to a smartphone, the smartphone collects a subject image indicating the subject placement of electrodes, and the smartphone sends the subject cardiogram and the subject image to the one or more computing systems.

In some aspects, the techniques described herein relate to a method performed by one or more computing systems for generating mappings of source electrocardiograms (ECGs) to target ECGs, the method including: accessing a plurality of heart configurations and ECG specifications, an ECG specification specifying a number of leads and a placement of one or more electrodes from which each lead is generated; for each heart configuration, running a simulation of electrical activity of a heart having that heart configuration; and for each combination of a heart configuration and an ECG specification, generating, from the simulated electrical activity of the simulation based on that heart configuration, a simulated ECG assuming that ECG specification; and storing a mapping that associates that heart configuration and that ECG specification to that generated simulated ECG. In some aspects, the techniques described herein relate to a method wherein each combination further includes a thorax configuration of a plurality of thorax configurations and wherein the simulated ECG is generated assuming that thorax configuration, and the mapping is further associated with that thorax configuration. In some aspects, the techniques described herein relate to a method further including generating a machine learning model using training data that includes, for each of the plurality of heart configurations, a simulated ECG based on an ECG specification of a mapping for that heart configuration labeled with a simulated ECG based on another ECG specification of a mapping for that heart configuration. In some aspects, the techniques described herein relate to one or more computing systems for synthesizing a synthesized cardiogram corresponding to a subject cardiogram of a subject, the one or more computing systems including one or more computer-readable storage mediums that store computer-executable instructions for controlling the one or more computing systems to access a machine learning (ML) model that inputs a source cardiogram and outputs a target cardiogram, the ML model being trained with training data that includes source cardiograms that are each labeled with a target cardiogram; receive a subject cardiogram; apply the ML model to the subject cardiogram; and output the target cardiogram output by the ML model; and one or more processors for controlling the one or more computing systems to execute one or more of the computer-executable instructions. In some aspects, the techniques described herein relate to one or more computing systems wherein the ML model is a convolutional neural network. In some aspects, the techniques described herein relate to a method performed by one or more computing systems for calculating body composition of a subject, the method including; receiving a scan of the body of the subject, the scan indicating distance from a scanner to locations on the body; receive weight of the subject; generating a three-dimensional (3D) representation of the body based on the scan; determining volume of the body based on the 3D representation; calculating a body fat percentage based on the weight and the volume; and displaying an indication of the body fat percentage as a presentation of the body composition of the subject. In some aspects, the techniques described herein relate to a method further including receiving scans of the body of the subject over time; for each scan, generating a 3D representation of the body based on the scan; and displaying a graphic based on the 3D representations to illustrate evolution of the shape of the body over time.

In some aspects, the techniques described herein relate to one or more computing systems including one or more computer-readable storage mediums that store a collection of source electrograms and target electrograms, each source electrogram based on a source placement of electrodes and each target electrogram based on a target placement of electrodes, wherein each target electrogram is associated with, for each of a plurality of source placements, a source electrogram; and computer-executable instructions for controlling the one or more computing systems to access a subject electrogram and a subject placement of electrodes; identify a source placement based on similarity to the subject placement; identify a source electrogram associated with the identified source placement based on similarity to the subject electrogram; designate the target electrogram that is associated with the identified source electrogram as a converted subject electrogram; and output the converted subject electrogram; and one or more processors for controlling the one or more computing systems to execute one or more of the computer-executable instructions. In some aspects, the techniques described herein relate to a method performed by one or more computing systems, the method including accessing a collection of mappings that each maps a source cardiogram to associated target cardiogram; identifying a source cardiogram based on similarity to a subject cardiogram; designating the target cardiogram associated with the identified source cardiogram as a synthesized subject cardiogram; and outputting the synthesized subject cardiogram. In some aspects, the techniques described herein relate to a method wherein the source cardiograms have a source number of one or more leads and the target cardiograms have a target number of one or more leads.

In some aspects, the techniques described herein relate to a method performed by one or more computing systems, the method including accessing a collection of simulated cardiograms, each simulated cardiogram having simulated leads, each simulated lead associated with a simulated placement of electrodes; accessing a subject cardiogram having subject leads, each subject lead associated with a subject placement of electrodes, wherein some of the simulated leads and the subject leads are common leads having the same placements; identifying a simulated cardiogram based on similarity to the subject cardiogram, the similarity based on the common leads; and designating a non-common lead of the identified simulated cardiogram as a synthesized lead; and outputting the synthesized lead.

All documents incorporated by reference are incorporated in their entirety for the full extent of their disclosures. In the event of inconsistencies between the language in this document and any incorporated-by-reference document, the language in the incorporated-by-reference document should be considered supplementary to that of this document and the language in this document controls.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. A method performed by one or more computing systems for converting a subject cardiogram based on a subject placement of electrodes to a converted subject cardiogram that is based on a target placement of electrodes, the method comprising:
   receiving the subject cardiogram and the subject placement of electrodes;
   accessing a collection of simulated source cardiograms and simulated target cardiograms, each simulated source cardiogram based on a source placement of electrodes and each simulated target cardiogram based on a target placement of electrodes, each simulated target cardiogram associated with, for each of a plurality of source placements, a simulated source cardiogram;
   identifying a source placement based on similarity to the subject placement;
   identifying a simulated source cardiogram associated with the identified source placement based on similarity to the subject cardiogram;
   designating the simulated target cardiogram that is associated with the identified simulated source cardiogram as the converted subject cardiogram; and
   outputting the converted subject cardiogram
   wherein each simulated source cardiogram is a nonstandard cardiogram based on a nonstandard placement of electrodes and each simulated target cardiogram is a standard cardiogram based on a standard placement of electrodes.

2. The method of claim 1 wherein each simulated target cardiogram and the associated simulated source cardiograms are generated based on a simulation of electrical activity of a heart based on a heart configuration of a plurality of heart configurations.

3. The method of claim 2 further comprising, prior to identifying a simulated source cardiogram, calibrating the collection based on similarity of the plurality of heart configurations to a subject heart configuration.

4. A method performed by one or more computing systems for converting a subject cardiogram based on a subject placement of electrodes to a converted subject cardiogram that is based on a target placement of electrodes, the method comprising:
   receiving the subject cardiogram and the subject placement of electrodes;
   accessing a collection of simulated source cardiograms and simulated target cardiograms, each simulated source cardiogram based on a source placement of electrodes and each simulated target cardiogram based on a target placement of electrodes, each simulated target cardiogram associated with, for each of a plurality of source placements, a simulated source cardiogram;
   identifying a source placement based on similarity to the subject placement;
   identifying a simulated source cardiogram associated with the identified source placement based on similarity to the subject cardiogram;
   designating the simulated target cardiogram that is associated with the identified simulated source cardiogram as the converted subject cardiogram; and
   outputting the converted subject cardiogram
   wherein each simulated target cardiogram and the associated simulated source cardiograms are generated based on a thorax configuration of a plurality of thorax configurations.

5. The method of claim 4 further comprising, prior to identifying a simulated source cardiogram, calibrating the collection based on similarity of the thorax configuration to a subject thorax configuration.

6. The method of claim 1 wherein the subject placement of electrodes is represented by an image of the electrodes after being placed.

7. The method of claim 1 wherein a cardiogram acquisition device collects the subject cardiogram and sends the subject cardiogram to a smartphone and the smartphone collects a subject image of the subject placement of electrodes and sends the subject cardiogram and the subject image to the one or more computing systems.

8. One or more computing systems for synthesizing a synthesized cardiogram based on a subject cardiogram of a subject, the one or more computing systems comprising:

one or more computer-readable storage mediums that store computer-executable instructions for controlling the one or more computing systems to:
access a collection of mappings that each maps a simulated source cardiogram to an associated simulated target cardiogram, the simulated source cardiograms and the simulated target cardiograms being generated based on simulations of electrical activity of a heart;
access a subject cardiogram;
identify a simulated source cardiogram based on similarity to the subject cardiogram;
designate the simulated target cardiogram associated with the identified simulated source cardiogram as a synthesized subject cardiogram; and
output the synthesized subject cardiogram
wherein each simulated source cardiogram and the associated simulated target cardiogram are associated with a thorax configuration of a plurality of thorax configurations; and
one or more processors for controlling the one or more computing systems to execute one or more of the computer-executable instructions.

9. The one or more computing systems of claim 8 wherein a simulated source cardiogram has three leads and a simulated target cardiogram has 12 leads.

10. The one or more computing systems of claim 8 wherein a simulated source cardiogram has multiple leads and a simulated target cardiogram has one lead.

11. The one or more computing systems of claim 8 wherein each simulated source cardiogram and the associated simulated target cardiogram are associated with a heart configuration of a plurality of heart configurations.

12. The one or more computing systems of claim 11 wherein the computer-executable instructions include instructions to, prior to identifying a simulated target cardiogram, calibrate the collection based on similarity of a subject heart configuration to the plurality of heart configurations.

13. The one or more computing systems of claim 8 wherein the computer-executable instructions include instructions to, prior to identifying a simulated source cardiogram, calibrate the collection based on similarity of a subject thorax configuration to the plurality of thorax configurations.

14. The one or more computing systems of claim 8 wherein the subject cardiogram is associated with a subject placement of electrodes, a simulated source cardiogram is associated with a source placement of electrodes of a plurality of source placements of electrodes, and the associated simulated target cardiogram is associated with a target placement of electrodes and wherein the identification of a simulated source cardiogram is further based on similarity of the subject placement to a source placement.

15. The one or more computing systems of claim 14 wherein a cardiogram acquisition device collects the subject cardiogram and sends the subject cardiogram to a smartphone, the smartphone collects a subject image indicating the subject placement of electrodes, and the smartphone sends the subject cardiogram and the subject image to the one or more computing systems.

16. One or more computing systems for synthesizing a synthesized cardiogram based on a subject cardiogram of a subject, the one or more computing systems comprising:
one or more computer-readable storage mediums that store computer-executable instructions for controlling the one or more computing systems to:
access a collection of mappings that each maps a simulated source cardiogram to an associated simulated target cardiogram, the simulated source cardiograms and the simulated target cardiograms being generated based on simulations of electrical activity of a heart;
access a subject cardiogram;
identify a simulated source cardiogram based on similarity to the subject cardiogram;
designate the simulated target cardiogram associated with the identified simulated source cardiogram as a synthesized subject cardiogram; and
output the synthesized subject cardiogram
wherein each simulated source cardiogram is a nonstandard cardiogram based on a nonstandard placement of electrodes and each simulated target cardiogram is a standard cardiogram based on a standard placement of electrodes; and
one or more processors for controlling the one or more computing systems to execute one or more of the computer-executable instructions.

* * * * *